United States Patent [19]

Brindley

[11] Patent Number: 5,015,825
[45] Date of Patent: May 14, 1991

[54] FURNACE FOR TENSILE/FATIGUE TESTING

[75] Inventor: Pamela K. Brindley, Strongsville, Ohio

[73] Assignee: The United States of America as represented by the United States National Aeronautics and Space Administration, Washington, D.C.

[21] Appl. No.: 382,885

[22] Filed: Mar. 19, 1990

[51] Int. Cl.⁵ .................. F27B 5/14; F27D 11/00; G01N 3/08; G01N 3/18
[52] U.S. Cl. ........................... 219/390; 73/826; 374/49; 374/50
[58] Field of Search ............ 219/390, 10.491; 374/49, 50; 73/800, 826

[56] References Cited

U.S. PATENT DOCUMENTS

| | | | |
|---|---|---|---|
| 2,154,280 | 4/1939 | Nadai et al. | 265/2 |
| 2,290,868 | 7/1942 | Eriksson | 73/51 |
| 2,375,032 | 5/1945 | Parke et al. | 73/95 |
| 2,534,980 | 12/1950 | Lubahn | 374/49 |
| 2,647,393 | 8/1953 | Stewart | 374/49 |
| 2,748,597 | 6/1956 | Kooistra | 73/15.6 |
| 3,100,253 | 8/1963 | O'Connor | 374/50 |
| 3,176,499 | 6/1965 | Sikora | 73/15.6 |
| 4,550,412 | 10/1985 | Holcombe et al. | 219/10.491 |

Primary Examiner—Bruce A. Reynolds
Assistant Examiner—Tuan Vinh To
Attorney, Agent, or Firm—Gene E. Shook; John R. Manning; James A. Mackin

[57] ABSTRACT

Mechanical properties of short test specimens are tested in tension and fatigue using an improved electrical resistance heating furnace having a short length that mounts between the grips of a typical testing machine. The furnace includes a ceramic inner liner having an oval cross-section to reduce heat loss at the ends. The furnace is divided into a plurality of individually controlled heating zones. Provision is made to supply an inert gas to the volume around the specimen in the center of the furnace.

20 Claims, 3 Drawing Sheets

FURNACE FOR TENSILE/FATIGUE TESTING

ORIGIN OF THE INVENTION

The invention described herein was made by an employee of the United States Government and may be manufactured or used by or for the Government without the payment of any royalties thereon or therefor.

TECHNICAL FIELD

This invention is concerned with a short furnace for heating flat specimens during mechanical property tests in tension and fatigue. The invention is particularly directed to a furnace that is small enough to fit between the grips of a typical mechanical testing machine without grip or load frame redesign.

Conventional furnaces are larger and longer than the furnace of the present invention in order to obtain the temperature profile desired of ±1% of the test temperature. These larger and longer furnaces incorporate circular cross sections which are characterized by excessive heat losses from the furnace ends.

In addition, prior art furnaces require long specimens which have lengths greater than typical short test specimens. Generally a minimum length of 8 inches is specified for the long specimens. The grips must be inside the furnace if these shorter specimens are to be tested in the longer furnaces. It is often questionable whether such an arrangement is adequate at some of the high temperatures required for testing. Some of these tests temperatures may go up to 1100° C., and the grip material will get hot enough to lose some of its strength at such high temperatures. Also, when testing unconventional materials which are not commercially available, such as many of the new intermetallic material composites, long lengths of material cannot be obtained. Thus, apparatus capable of heating short specimens must be provided.

Prior art furnaces do not use multi-zones in such a small height furnace. From a practical nature, a shorter furnace which will fit between the grips is not commercially available. Therefore, there is no way to use the grips as cold grips and provide an acceptable temperature gradient over the gage.

It will be appreciated that smaller specimen configurations can be tested in commercially available prior art furnaces when the testing is in compression. Such compression testing is a different procedure and is not included as a testing mode compatible with the testing contemplated by the present invention.

It is, therefore, an object of the present invention to provide a short furnace that can be used to heat flat specimens for mechanical property tests in tension and fatigue.

Another object of the invention is to provide a short furnace that fits between the grips of a typical mechanical testing machine.

A still further object of the invention is to provide a furnace having an acceptable temperature profile within the gage section of the sample because of its cross sectional shape and multi-zone design.

BACKGROUND ART

U.S. Pat. Nos. 2,154,280 and 2,748,597 to Nadai et al and Kooistra, respectively, disclose testing materials under increased temperature by employing a covering furnace.

U.S. Pat. No. 2,290,868 to Eriksson is concerned with a tensile strength apparatus that employs a covering furnace with an oval-like cross section for receiving the test specimen.

U.S. Pat. No. 2,375,032 to Park et al and U.S. Pat. No. 3,176,499 to Sikora described tensile testing apparatus with covering furnaces that employ lines or pipes to feed an inert gas or means to evacuate the chamber.

DISCLOSURE OF THE INVENTION

This invention is concerned with an improved electrical resistance heater furnace having a short length. A ceramic liner having a generally oval cross section is employed to cover a test specimen for tensile testing. A metal jacket with inlet lines for electric heater wires covers the liner. Orifices for an inert gas line and extensometer probes are also provided in the jacket.

The furnace is particularly useful in heating flat specimens during mechanical property tests in tension and fatigue.

BRIEF DESCRIPTION OF THE DRAWINGS

The objects, advantages and novel features of the invention will be more fully apparent from the following detailed description when read in connection with the accompanying drawings in which.

BEST MODE FOR CARRYING OUT THE INVENTION

Figure 1:
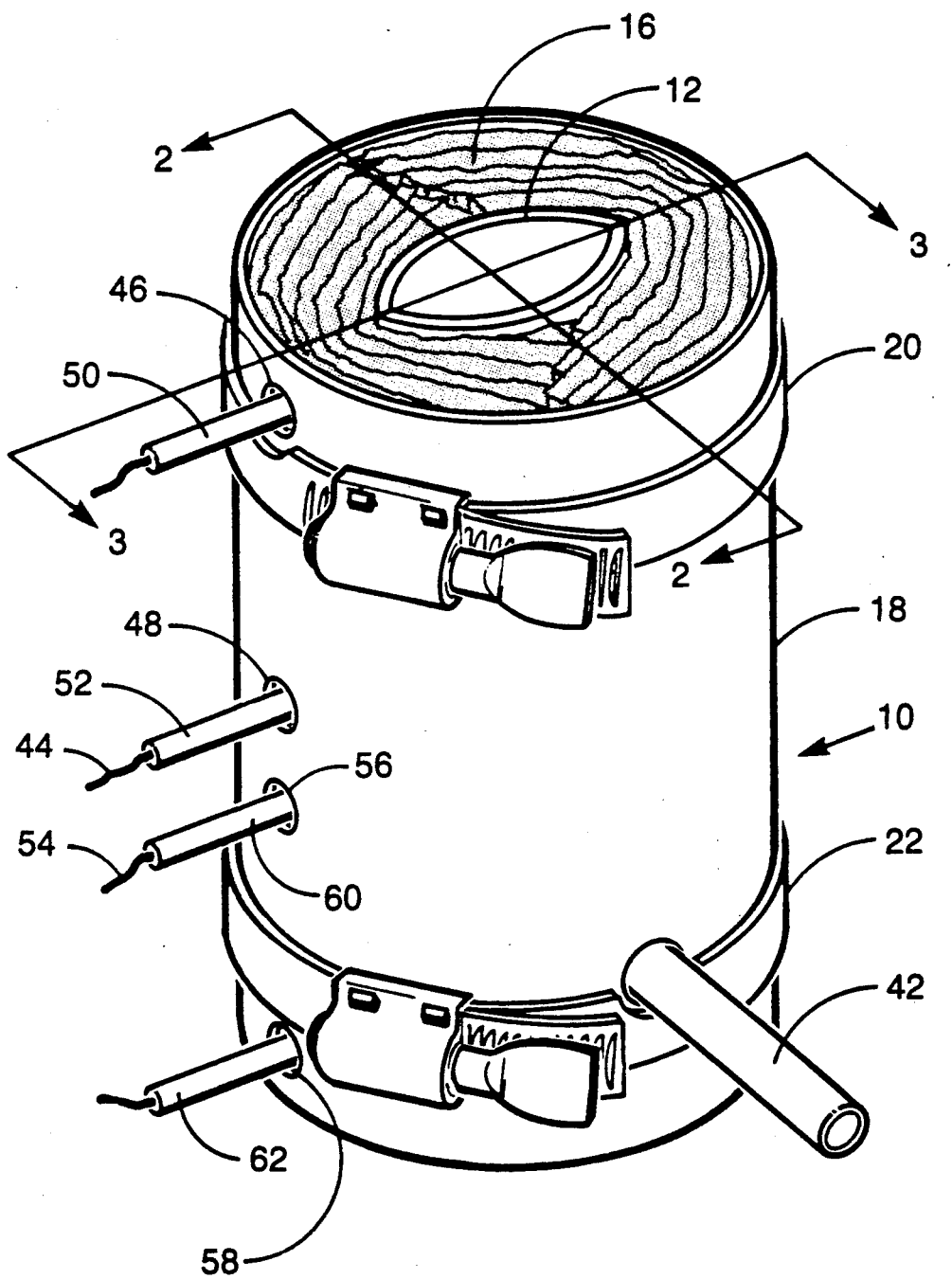
FIG. 1 is a perspective view of a short furnace constructed in accordance with the present invention.
Figure 2:
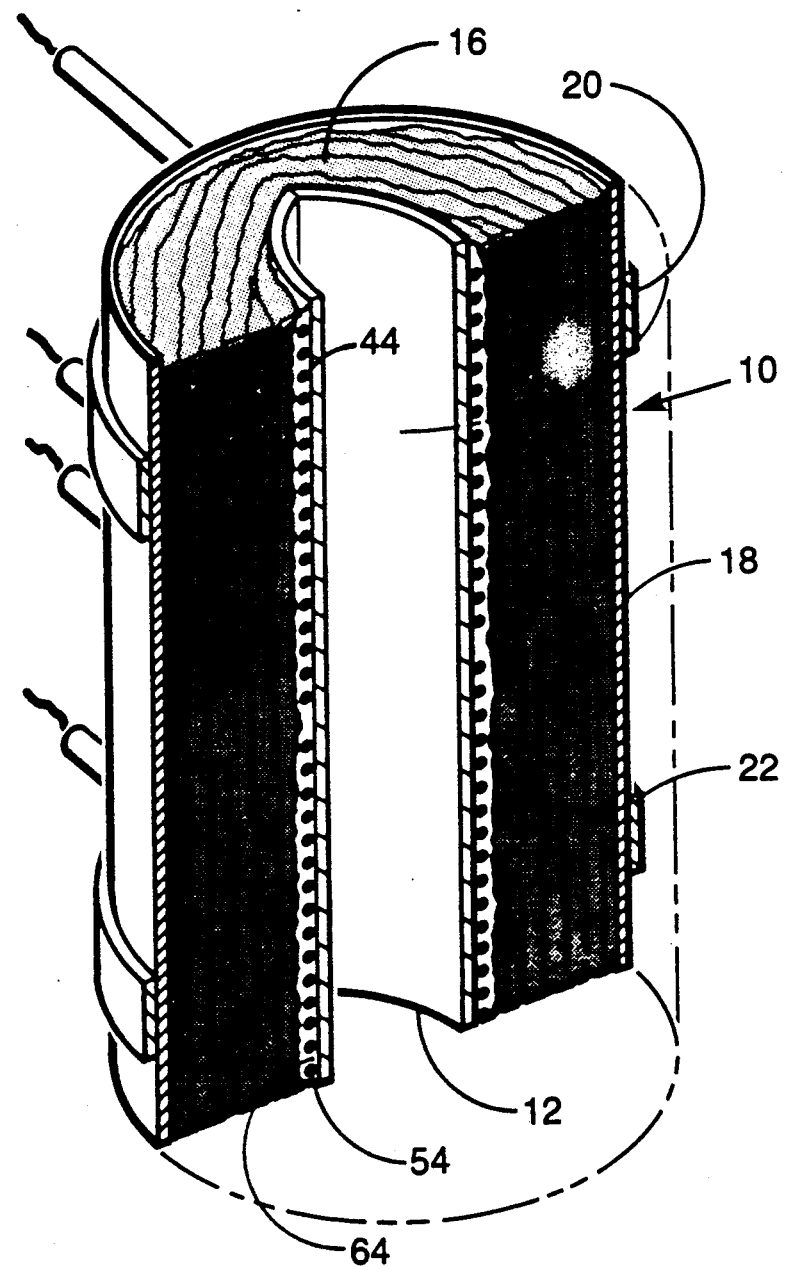
FIG. 2 is a perspective vertical half-section view of a short furnace taken along the line 2—2 in FIG. 1.
Figure 3:
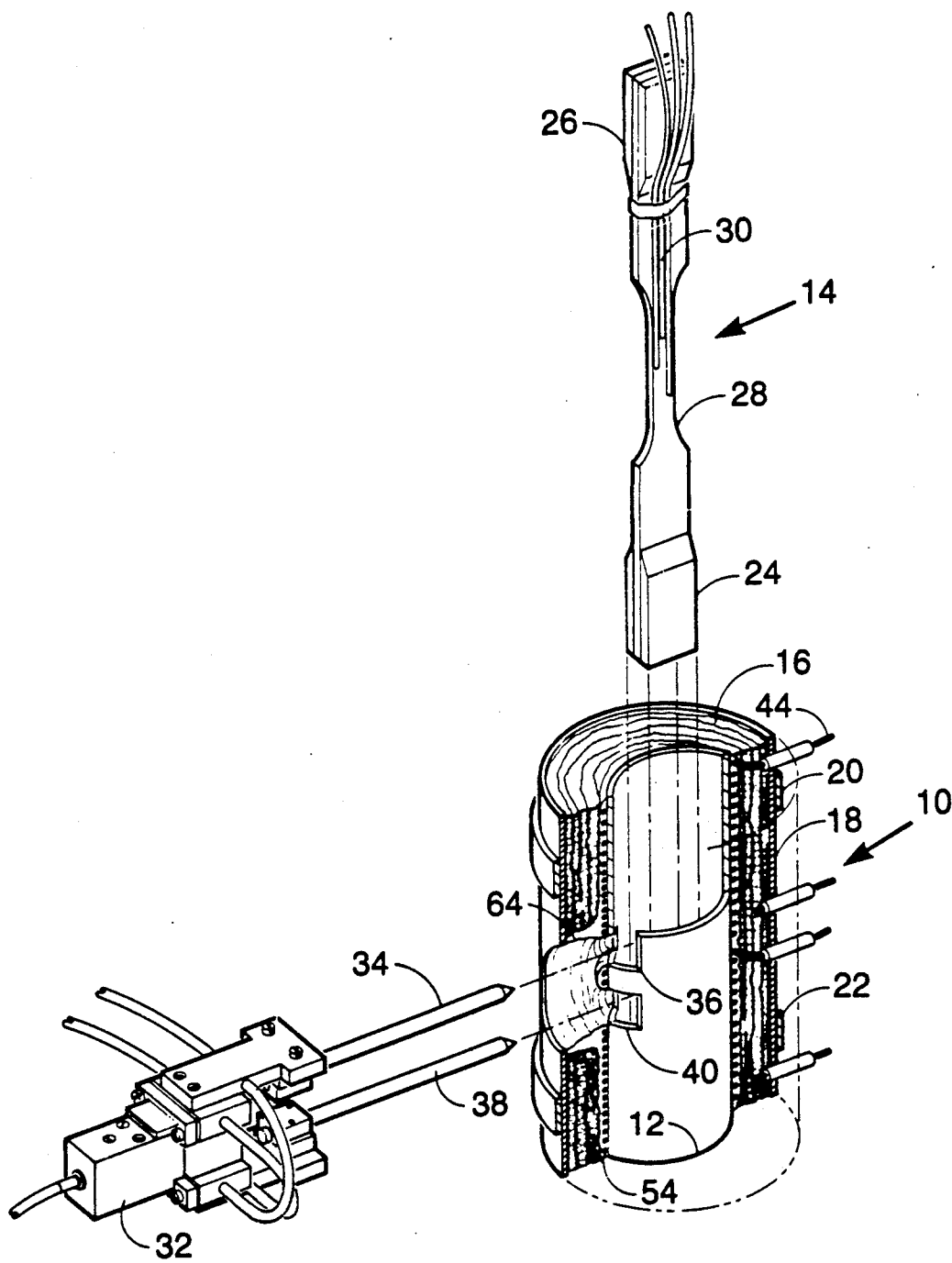
FIG. 3 is a perspective vertical half-section view taken along the line 3—3 in FIG. 1 showing the short furnace with a test specimen and an extensometer.

Referring now to the drawings there is shown in FIGS. 1, 2 and 3, a resistance type short furnace 10 constructed in accordance with the present invention. The furnace utilizes an inner liner 12 of a suitable ceramic material such as mullite or alumina. The liner 12 is oval in cross-section to cover a flat specimen 14 as shown in FIG. 3 during mechanical property tests in tension and fatigue without excessive heat loss at the ends.

A suitable insulating material 16 such as low density alumina mat or zirconia surrounds the liner 12. A metal jacket 18 encircles this insulating material, and the jacket is maintained in position by a pair of adjustable bands 20 and 22. The jacket 18 is preferably of stainless steel. The jacket 18 and liner 12 are both short having lengths between 3.1875 inches and 3.60 inches. Thus, the furnace 10 fits between the grips of a typical mechanical testing machine without redesigning either the grips or the load frame.

Referring to FIG. 3 the specimen 14 passes through the furnace 10 so that the lower grip (not shown) of the testing machine clamps onto a lower tab 24 while an oppositely disposed upper tab 26 is clamped by the upper grip (not shown) of the testing machine. This positions the centrally disposed gage section 28 of the specimen 14 in the central portion of the furnace 10. A plurality of thermocouples 30 engage this gage section 28.

An extensometer 32 is mounted adjacent to the furnace 10 at approximately its midpoint. An upper probe 34 extends through a suitable opening in the jacket 18 through an aperture 36 in the liner 12 so that it contacts the edge of the gage section 28 of the specimen 14.

Likewise, a lower probe 38 that is spaced from the upper probe 34 a predetermined distance extends through the jacket 18 and insulation 16 and a suitable aperture 40 in the liner 12. The lower probe 38 likewise contacts the edge of the specimen gage section 28.

As shown in FIG. 1, provision is made to supply an inert gas to the volume around the specimen 14 within the liner 12 through a ceramic tube 42. A suitable inert gas source is connected to the tube 42 which passes to the interior of the liner 12.

As best shown in FIGS. 2 and 3 the furnace is divided into a pair of heating zones. A first resistance heating wire 44 passes through a pair of openings 46 and 48 in the jacket 18 as shown in FIG. 1. The resistance heating wire 44 is preferably of platinum and passes through the insulation 16 where it is wrapped around the liner 12 as shown in FIGS. 2 and 3.

A ceramic insulator 50 surrounds the wire 44 and passes through the opening 46 so that the wire 44 is insulated from the metal jacket 18 as shown in FIG. 1. In a like manner, a similar ceramic insulator 52 surrounds the wire 44 and passes through the opening 48 to insulate the wire 44 from the metal jacket 18. The wire 44 is connected to a suitable power supply (not shown) to form the first or upper heating zone that is individually controlled.

A resistance heating wire 54 passes through a pair of spaced openings 56 and 58 in the jacket 18. This wire 54 passes through the insulation 16 and encircles the liner 12. A tubular insulator 60 surrounds the wire 54 and passes through the opening 56 to insulate the wire 54 from the jacket 18. A similar tubular insulator 62 passes through the opening 58 to insulate the wire 54 from the jacket 18. The wire 54 is connected to a suitable power supply (not shown) to form a second or lower heating zone that is individually controlled.

The windings of both of the resistance heating wires 44 and 54 extend both around the liner 12, as well as back and forth across the surface of the liner to provide heat where it is needed. More particularly, higher density windings are provided in areas of greater heat losses, such as the ports 36 and 40 for the extensometer probes 34 and 38, or the opening around the inert gas tube 42. As shown in FIG.. 2 and 3 the wires 44 and 54 are held in their proper positions by a suitable ceramic cement 64.

It is apparent that the furnace 10 is small enough that short flat specimens 14 may be tested using cold grips for clamping the tabs 24 and 26. The furnace 10 provides a temperature profile of ±1% of the test temperature up to 1100° C. through the use of separate controls for the multi-zones of windings.

It is further contemplated that the furnace can also be wound for resistance heating with any material, including platinum, that can be bent or machined into a desired configuration. The coil pattern of the winding is dependent on the location of the ports and the density windings needed to overcome heat loss associated with ports through the furnace. Any ports or openings for various types of equipment may be used. It is apparent that the maximum use temperature of the furnace is limited only by the type of material used in the windings.

While the preferred embodiment of the invention has been shown and described it will be apparent that various structural modifications may be made to the furnace without departing from the spirit of the invention and the scope of the subjoined claims. By way of example, the furnace 10 is particularly useful for testing any material which is short and flat in configuration. The furnace 10 can also be used to test typical specimens having lengths that are equal to or greater than 8 inches and have any cross-sectional design which can fit through the liner 12.

I claim:

1. A furnace for heating a test specimen having a centrally disposed substantially flat gage section between oppositely disposed tabs during mechanical property testing in tension and fatigue comprising a non-cylindrical liner covering said flat gage section while leaving said tabs exposed, said liner having a non-circular oval cross-section defined by a major dimension and a minor dimension wherein portions of said liner adjacent to the ends of said major dimension are in close proximity to the edges of said flat gage section and other portions of said liner adjacent to the ends of said minor dimension being in close proximity to the surfaces of said flat gage section thereby minimizing heat loss at the ends of the liner adjacent to said tabs during testing, an insulating material surrounding said liner, a cylindrical jacket surrounding said insulating material for enclosing the same, said jacket and said liner having substantially the same length which is less than the spacing between the test specimen tabs, means for supplying a gas to the interior of said liner, and at least two heating wires encircling said liner to form at least a pair of heating zones.

2. A furnace as claimed in claim 1 wherein the liner is a ceramic material.

3. A furnace as claimed in claim 2 wherein the liner is selected from the group consisting essentially of mullite and alumina.

4. A furnace as claimed in claim 1 wherein the jacket and liner have lengths between about 3.1875 inches and 3.60 inches.

5. A furnace as claimed in claim 1 wherein the insulating material surrounding the liner is selected from the group consisting essentially of alumina and zirconia.

6. A furnace as claimed in claim 5 wherein the jacket is metal.

7. A furnace as claimed in claim 6 wherein the jacket is stainless steel.

8. A furnace as claimed in claim 1 wherein an inert gas is supplied to the interior of the liner.

9. In a resistance heating furnace of the type used to heat a test specimen having a centrally disposed substantially flat gage section between oppositely disposed tabs during mechanical testing in tension and fatigue, the improvement comprising a plurality of heating wires wound around said test specimen forming a plurality of heating zones with the density of the windings being higher in predetermined areas, and a ceramic member interposed between said heating wires and said test specimen for covering the same, said member having a length which is less than the spacing between said tabs to cover said gage section while leaving said tabs exposed and a generally oval cross-section defined by a major dimension and a minor dimension wherein portions of said member adjacent to the ends of said major dimension are in close proximity to the edges of said flat gage section and portions of said member adjacent to the ends of said minor dimension being in close proximity to the surfaces of said flat gage section to minimize heat loss at the ends thereof.

10. A furnace as claimed in claim 9 wherein the ceramic member is a material selected from the consisting essentially of mullite and alumina.

11. A furnace as claimed in claim 10 wherein the ceramic member comprises a liner having a plurality of openings therein for said heating wires,
   a layer of insulating material surrounding said liner, and
   a jacket surrounding said insulating material for enclosing the same.

12. A furnace as claimed in claim 11 wherein the insulating material surrounding the liner is selected from the group consisting essentially of alumina and zirconia.

13. A furnace as claimed in claim 11 wherein the jacket is metal.

14. A furnace as claimed in claim 13 wherein the jacket is stainless steel.

15. A furnace as claimed in claim 9 including means for supplying an inert gas to the interior of the ceramic member.

16. A furnace as claimed in claim 9 wherein the ceramic member has a length between about 3.1875 inches and 3.60 inches.

17. In combination with an extensometer having a pair of spaced probes for contacting an edge of a centrally disposed substantially flat gage section of a test specimen having a tab at each end of said gage section, a furnace having a plurality of zones for heating said gage section during mechanical property testing of said specimen in tension and fatigue comprising a non-cylindrical liner covering said gage section while leaving said tabs exposed, said liner having centrally disposed spaced apertures for receiving said extensometer probes and a non-circular cross-section defined by a major dimension and a minor dimension wherein portions of said liner adjacent to the ends of said major dimension are in close proximity to the edges of said flat gage section with said apertures being positioned at said major dimension and other portions of said liner adjacent to the end of said minor dimension being in close proximity to the surfaces of said flat gage section whereby heat loss at the ends of the liner adjacent to said tabs is minimized, an insulating material surrounding said liner, a cylindrical jacket surrounding said insulating material and said non cylindrical liner, said jacket and said liner having substantially the same length, a tube extending from said jacket through said insulating material to the interior of said liner for conducting an inert gas to the interior of said liner adjacent to said flat gage section, and a plurality of resistance heating wires encircling adjacent portions of said liner thereby forming said heating zones, each of said heating wires extending outward through openings in said jacket.

18. A furnace as claimed in claim 17 wherein the liner is a ceramic material.

19. A furnace as claimed in claim 19 wherein the insulating material surrounding the liner is selected from the group consisting essentially of alumina and zirconia.

20. A furnace as claimed in claim 17 wherein the cylindrical jacket is metal.

* * * * *